US008257285B2

(12) United States Patent
Cook

(10) Patent No.: US 8,257,285 B2
(45) Date of Patent: Sep. 4, 2012

(54) TRACTION BED WITH VIBRATOR ASSEMBLY

(76) Inventor: Gerry Cook, Sandpoint, ID (US)

( * ) Notice: Subject to any disclaimer, the term of this patent is extended or adjusted under 35 U.S.C. 154(b) by 820 days.

(21) Appl. No.: 12/587,897

(22) Filed: Apr. 6, 2009

(65) Prior Publication Data

US 2010/0137759 A1 Jun. 3, 2010

Related U.S. Application Data

(60) Provisional application No. 61/123,528, filed on Apr. 9, 2008.

(51) Int. Cl.
*A61H 1/00* (2006.01)
*A61F 5/00* (2006.01)

(52) U.S. Cl. .............. 601/46; 602/32; 602/36; 606/237; 606/240; 601/23; 601/56; 5/915

(58) Field of Classification Search .............. 602/32–40; 128/845; 606/237, 240–242; 601/23–25, 601/46, 49, 56–59; 5/915, 621–624
See application file for complete search history.

(56) References Cited

U.S. PATENT DOCUMENTS

| | | | | |
|---|---|---|---|---|
| 2,822,805 | A * | 2/1958 | Hill | 606/242 |
| 3,638,646 | A | 2/1972 | Draux | |
| 3,830,233 | A | 8/1974 | Hill | |
| 3,868,951 | A | 3/1975 | Albrecht | |
| 4,230,098 | A | 10/1980 | Uematsu | |
| 4,579,109 | A * | 4/1986 | Lundblad | 606/243 |
| 4,582,050 | A | 4/1986 | Willis | |
| 5,010,880 | A | 4/1991 | Lamb | |
| 5,052,378 | A * | 10/1991 | Chitwood | 606/242 |
| 5,135,537 | A | 8/1992 | Lamb | |
| 6,108,838 | A | 8/2000 | Connolly et al. | |
| 6,123,680 | A | 9/2000 | Brummer | |
| 6,319,213 | B1 | 11/2001 | Tomac | |
| 6,328,759 | B1 * | 12/2001 | Zhang | 606/242 |
| 6,536,056 | B1 | 3/2003 | Vizalik et al. | |
| 6,892,405 | B1 | 5/2005 | Dimitriu et al. | |
| 6,904,631 | B2 | 6/2005 | Vizalik et al. | |
| 7,112,215 | B2 | 9/2006 | Xiao et al. | |
| 7,346,945 | B2 | 3/2008 | Phillips et al. | |
| 2003/0208847 | A1 | 11/2003 | Vrzalik et al. | |
| 2005/0192517 | A1 | 9/2005 | Becerra et al. | |
| 2005/0229321 | A1 | 10/2005 | Phillips et al. | |
| 2006/0161084 | A1 * | 7/2006 | Henke | 602/32 |
| 2006/0178607 | A1 | 8/2006 | Evans | |
| 2006/0287619 | A1 | 12/2006 | Becerra et al. | |
| 2006/0293156 | A1 | 12/2006 | Trees | |

* cited by examiner

*Primary Examiner* — Patricia Bianco
*Assistant Examiner* — George N Phillips
(74) *Attorney, Agent, or Firm* — Richard C. Conover

(57) ABSTRACT

A traction bed having a planar table on which a patient may lie with the head disposed at one end and the feet disposed at the other end. A vibration platform is disposed on the planar table for imparting vibration motion to the patient. A pelvic belt is fitted on the patient and a first strap is connected to one side of the pelvic belt and a second strap is connected to the second side of the pelvic belt. Apparatus is included for selectively applying a tension force to the first and second straps in a direction toward the foot end of the table. Further, a chest harness is fitted on the patient and includes a pair of shoulder straps extending toward the head end of the table. Apparatus is provided for selectively applying a tension force to both shoulder straps toward the head end of the table.

6 Claims, 9 Drawing Sheets

TRACTION BED WITH VIBRATOR ASSEMBLY

This application claims the benefit of provisional application Ser. No. 61/123,528 filed Apr. 9, 2008.

BACKGROUND OF INVENTION

The present invention relates to a traction bed incorporating a vibration assembly. The traction bed provides apparatus for creating a disparate pull between head and foot and also a disparate pull on either side of patient lying on the traction bed.

Many traction tables are known which apply orthopedic traction. For example, U.S. Pat. No. 5,010,880 to Lamb describes a traction device on which a patient lies and traction forces are applied to the neck of the patient. See also U.S. Pat. No. 3,868,951 to Albrecht which shows another traction device.

There are many spinal conditions which require treatment. For example, a patient may have a posterior lateral disc bulge, a posterior lateral herniation, a sciatic nerve impingement, or a scoliosis condition requiring treatment. None of the known traction devices are as versatile as the present invention which allows orthopedic treatment of the many spinal conditions.

It is an object of the present invention to provide a versatile traction bed which provides a disparate pull between head and foot and also a left to right imbalance thus enabling a user treating the patient to apply different forces on the spine to correct the problem being treated.

SUMMARY OF INVENTION

The present invention relates to a traction bed having an elongate planar table on which a patient may lie with the head disposed at one end and the feet disposed at the other end. A vibration platform is disposed on the planar table for imparting vibration motion to a patient lying on the table. A pelvic belt is fitted on the patient and a first strap is connected to one side of the pelvic belt and a second strap is connected to the second side of the pelvic belt. Apparatus is included for selectively applying a tension force to the first strap in a direction toward the foot end of the table and apparatus is provided for applying a tension force to the second strap in a direction toward the foot end of the table. Further, a chest harness is fitted around the chest of the patient and includes a pair of shoulder straps extending toward the head end of the table. Apparatus is provided for selectively applying a tension force to one of the shoulder straps toward the head end of the table and apparatus is also provided for selectively applying a tension force to the other shoulder strap toward the head end of the table.

BRIEF DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF A PREFERRED EMBODIMENT

Figure 1:
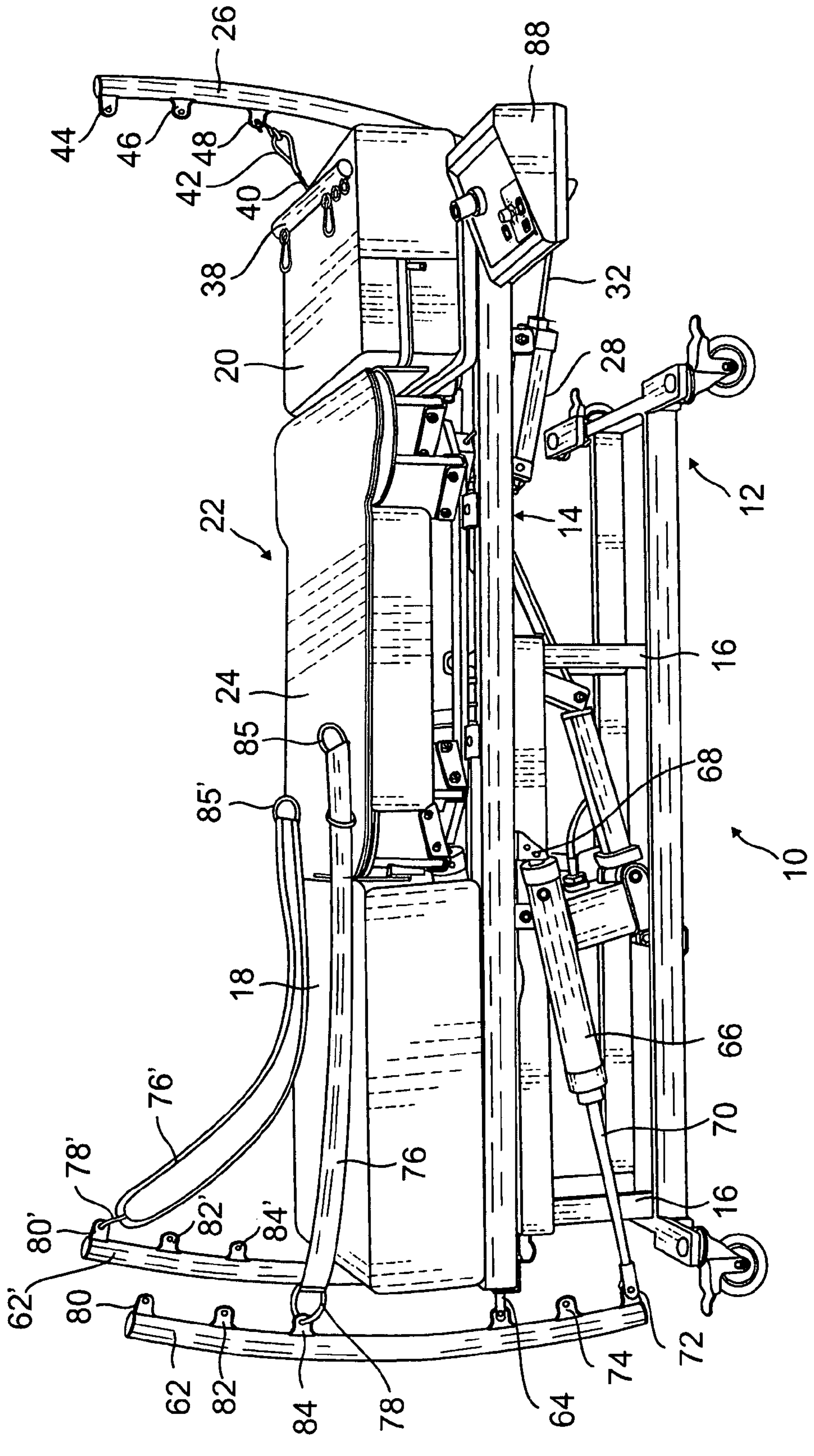
FIG. 1 is a perspective elevational view of a traction bed according to the present invention.

A traction bed 10, according to the present invention, is shown in FIG. 1. The traction bed 10 includes a wheeled lower frame assembly 12 and an upper frame assembly 14. The upper frame 14 is mounted in spaced apart relation with the lower frame 12 with upright supports 16. A cushion 18 is placed on the upper frame 14 at the foot of the traction bed 10. A cushion 20 is placed on the upper frame 14 at the head of the traction bed 10. A vibration apparatus 22 is positioned on top of the frame 14 and bolted thereto at a position between cushions 18 and 20. In a preferred embodiment, the vibration apparatus includes the therapeutic vibration apparatus as shown and described in International Publication Number WO 2005/067860 which was published Jul. 28, 2005. The vibration apparatus 22 includes a vibration platform 24 which is aligned with the top surfaces of the cushions 18 and 20. When the vibration apparatus is actuated, the vibration platform 24 vibrates in a manner as described in International Publication Number WO 2005/067860.

Figure 2:
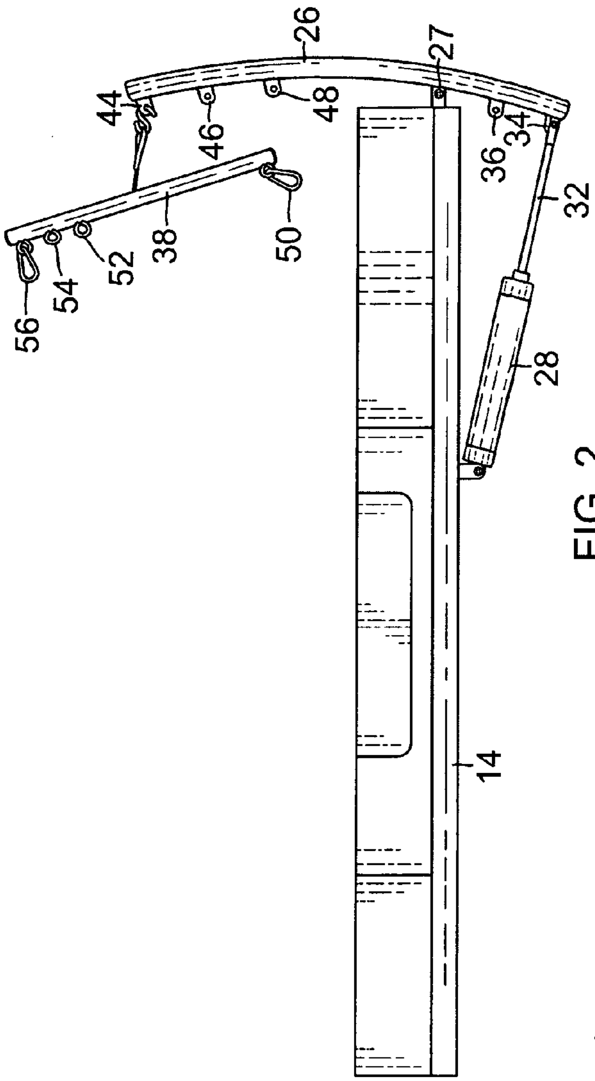
FIG. 2 is a schematic view of a pivot arm and spreader bar used at the head end of the traction bed shown in FIG. 1.

At the head of the traction bed 10, a pivot arm 26 is pivotally mounted to upper frame 14 at a center pivot 27 as schematically shown in FIG. 2. A conventional double acting pneumatic cylinder 28 has one end pivotally mounted to the upper frame 14 at 30 as shown in FIG. 2. The pneumatic cylinder 28 pneumatically extends or retracts a shaft 32 connected to an interior piston (not shown) in pneumatic cylinder 28. The distal end of the shaft 32 may be connected to one of a plurality of attachment points 34 and 36 provided on the arm 26.

Figure 3:
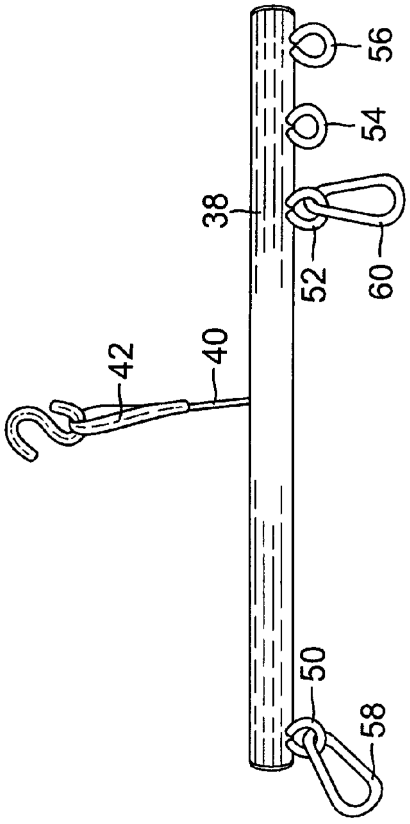
FIG. 3 is an elevational view of the spreader bar shown in FIGS. 1 and 2.

A spreader bar 38 as shown in FIGS. 2 and 3 includes a cable 40 connected to a carabiner 42 as shown in FIGS. 2 and 3. The carabiner 42 is used for connecting the spreader bar 38 to one of a plurality of attachment points 44, 46 and 48, formed on the pivot arm 26.

The spreader bar 38 includes an attachment point 50 located at one end of the spreader bar 38 as shown in FIG. 3 and further includes a series of spaced apart attachment points 52, 54 and 56 formed on the spreader bar 38 at the opposite at the end of spreader bar 38 opposite attachment point 50. A carabiner 58 is attached to the attachment point 50 and is used for attaching the spreader bar 38 to a shoulder strap of a harness fitted on a patient as will be subsequently described. A second carabiner 60 is provided for connecting one of the attachment points 52, 54 or 56 to another shoulder strap of a harness fitted on a patient as will be subsequently described.

Figure 4:
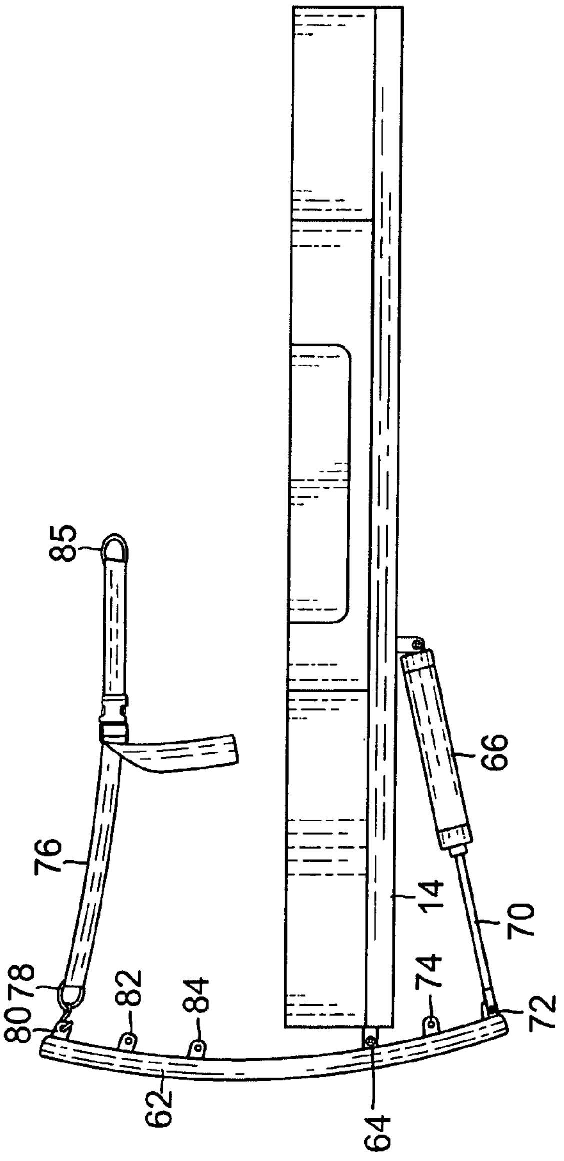
FIG. 4 is a schematic view of a pivot arm used at the foot end of the traction bed shown in FIG. 1.

A pivot arm 62 is pivotally mounted to the foot end of upper frame 14 at a center pivot 64 as shown in FIG. 1 and schematically in FIG. 4. A conventional double-acting pneumatic cylinder 66 has one end pivotally mounted to the upper frame 14 at 68 as shown in FIGS. 1 and 4. The pneumatic cylinder 66 pneumatically extends or retracts a shaft 70 connected to an interior piston (not shown) in pneumatic cylinder 66. The distal end of the shaft 70 may be connected to one of a plurality of attachment points 72 and 74 provided on the pivot arm 62. A strap 76 has a carabiner 78 provided at one end thereof. The carabiner 78 is used for connecting the strap 76 to one of a plurality of attachment points 80, 82 and 84 formed on arm 62. The strap 76 is also provided with a carabiner 85 located at an end of strap 76 opposite carabiner 78. The carabiner 85 is used for attaching the strap 76 to a pelvic belt 100 fitted on the patient as will be subsequently described.

Similarly, a second pivot arm 62' is connected to the foot end of upper frame 14. A second pneumatic cylinder (not shown) similar to pneumatic cylinder 66 has a shaft 70' connected to one of a plurality of attachment points 72' and 74' provided on pivot arm 62'. Also, in a similar manner, a strap 76' is connected with a carabiner 78' to one of the attachment points 80', 82' and 84' located on pivot arm 62' and with carabiner 85' to pelvic belt 100.

Figure 5:
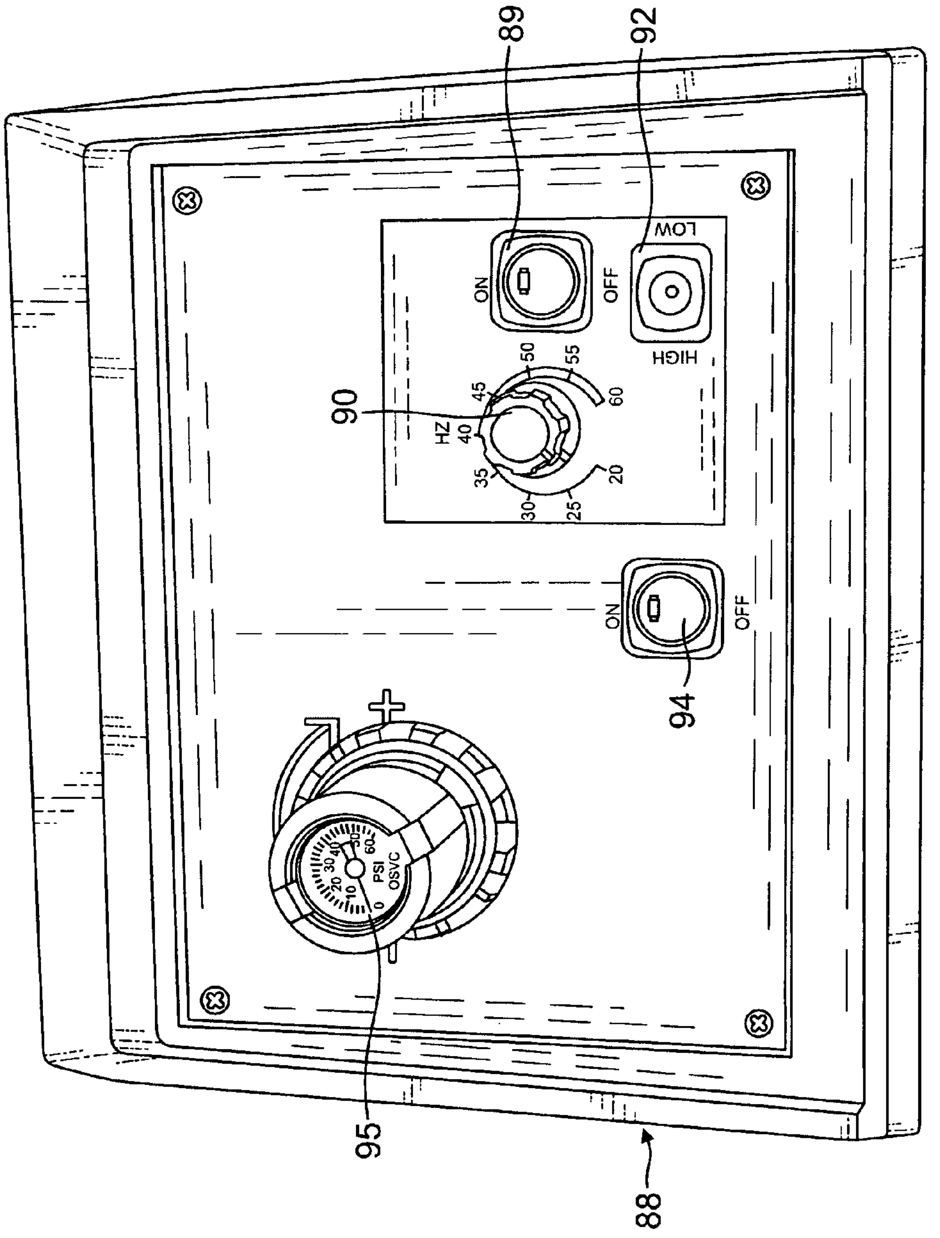
FIG. 5 is a top perspective view of a control panel shown in FIG. 1.

A control panel 88 is mounted to the upper frame 14 as shown in FIG. 1. The control panel is shown in detail in FIG. 5. The control panel includes an electrical on/off switch 89 for actuating the vibrator assembly 22 and an electrical dial switch 90 which is electrically connected to the vibrator assembly 22 for selecting the frequency of the vibration. A toggle switch 92 is electrically connected to the vibration assembly 22 and in one position the amplitude of vibration is set at a low position and in a second toggle position the amplitude is set to a high amplitude.

The control panel 88 also includes an on/off switch 94 which is electrically connected to a pneumatic air supply for the pneumatic cylinders 28, 66 and 66'. When the switch 94 is turned “on” the pneumatic cylinder 28 and the two pneumatic cylinders 66 and 66' simultaneously cycle the pivot arms 26, 62 and 62' in a back and forth movement. When the top portion of the pivot arms 26, 62 and 62' are pivoted away from the bed, this movement causes the spreader bar 38 to be moved away from the cushion 20 and also the straps 76 and 76' to draw against the pelvic belt of the harness fitted on a patient thereby applying a traction force to a patient lying on the bed. The control panel includes conventional circuitry (not shown) which cycles the simultaneous extension and retraction of shafts 32 and 70 at a predetermined frequency. The control panel 88 further includes a pressure gauge 95 which provides a visual indication of the air pressure within the pneumatic cylinders.

Figure 6:
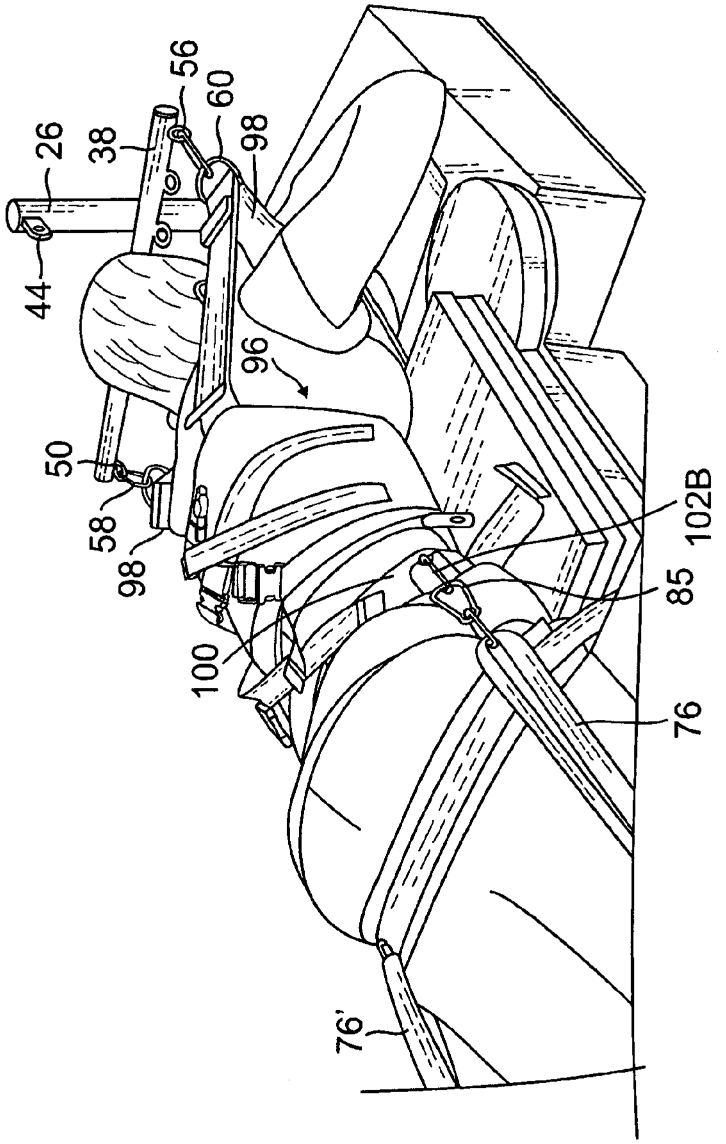
FIG. 6 is a perspective view of the present invention with a patient lying stomach down on the traction bed.
Figure 7:
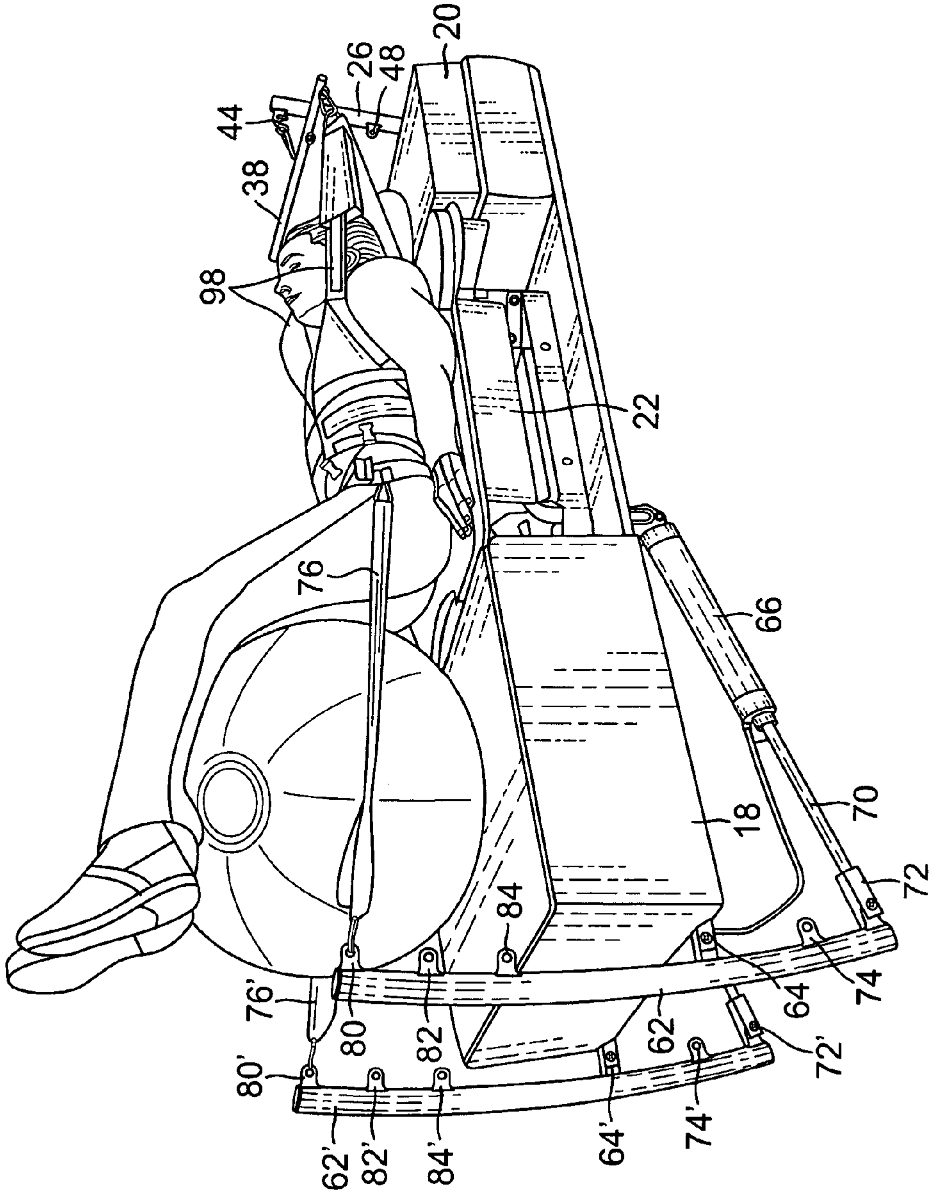
FIG. 7 is a perspective view of the present invention with parts removed and with a patient lying back down on the traction bed.

In operation, the traction bed 10 is used by having a patient lie on the cushions 18 and 20 and the vibration apparatus 22 and shown in FIGS. 6 and 7. The patient has a chest harness 96 fitted on the patient. The chest harness 96 has a pair of shoulder straps 98. The carabiner 58 is used for connecting a “D” -ring on one of the shoulder straps 98 to the attachment point 50 of spreader bar 38. The carabiner 60 is used for connecting the other shoulder strap 98 to one of the attachment points 52, 54 or 56 of the spreader bar 38. The attachment point 52 is positioned for maximum traction. The attachment point 54 is positioned for medium traction and the attachment 56 is positioned for minimal traction. The carabiner 42 attached to the spreader bar 38 is used for connecting the spreader bar 38 to the pivot arm 26 at one of the attachment points 44, 46 or 48. Attachment point 48 is positioned for maximum traction. Attachment point 46 is positioned for medium traction. Attachment point 44 is positioned for minimal traction.

Figure 8:
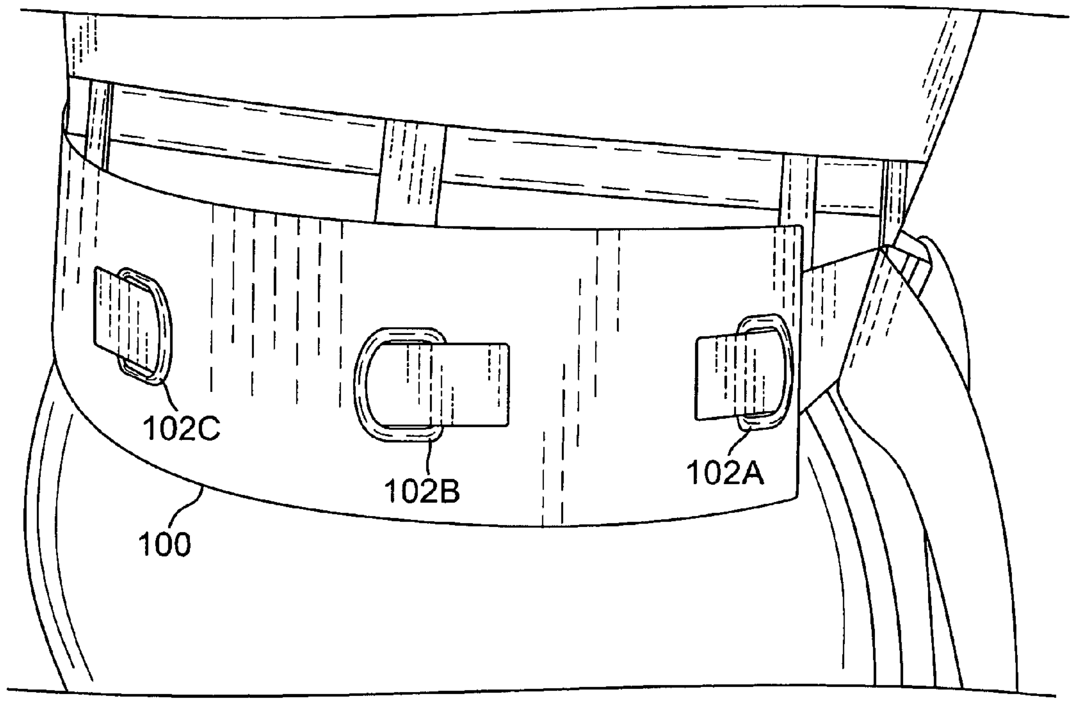
FIG. 8 is a perspective view and description of a pelvic belt used with the present invention.

A pelvic belt 100 is fitted around the pelvis of the patient. The pelvic belt 100 has three “D” rings, namely, 102A for an anterior attachment, 102B for a neutral attachment and for a posterior attachment, and 102C for a posterior attachment. These “D” rings 102A, 102B and 102C are located on one side of the pelvic belt 100 as shown in FIG. 8. The other side of the pelvic belt 100 has three “D” rings 102A', 102B' and 102C' (not shown) similarly positioned. The particular “D” rings selected for attachment with the pivot arms 62 and 62' are selected for the type of treatment to be given to a patient. For example, if the carabiner 85 is used to connect the strap 76 to the “D” ring 102A and the carabiner 85' is used to connect the strap 76' to a “D” ring 102C', this will cause counter torque on the ilium around the sacrum along the sagittal plane. Other connections can be used to achieve different results.

The carabiner 78 is used for connecting the strap 76 to one of the attachment points 80, 82, or 84 of pivot arm 62. The attachment point 80 is positioned for minimum traction. The attachment point 82 is positioned for medium traction. The attachment point 84 is positioned for maximum traction. Similarly, the carabiner 78' is used for connecting the strap 76' to the pivot arm 62' in a similar manner.

The shaft 70 of the pneumatic cylinder 66 is attached to one of the attachment points 72 or 74 of pivot arm 62. The attachment point 72 is positioned for maximum traction and the attachment 74 is positioned for minimal traction. Similarly, the shaft 70' of the pneumatic cylinder 66' located on the opposite side of traction bed 10 is connected to the pivot arm 62' in a similar manner.

The traction bed 10, according to the present invention, is very flexible. Equal forces can be applied to the shoulder and pelvis of the patient or if it desirable to have a disparate pull between the shoulder and the pelvis, this can also be achieved. Further, a left to right imbalance can also be achieved. For example, if a posterior lateral disk bulge is to be treated and it is desired to maximize the pull opposite the bulge, this is accomplished by rotating the spreader bar 38 so that the attachment points 52, 54 and 56 are positioned on the side of the patient where maximum pull is to occur. Then if carabiner 60 is connected to attachment point 52 and the shoulder strap 98 on the side of the patient where maximum pull is to occur and the carabiner 58 is attached to attachment point 50 and the other shoulder strap 98, the force acting on the side to be treated is effectively doubled versus the force acting on the attachment point 50 side.

With this device, various back problems can be treated. For example, a posterior/lateral herniation can be treated by setting a greater pull on the side opposite the bulge and maximizing the anterior opening with an intermittent pull/relay to create a billows effect and bring the disk bulge back into a center position. Further a sciatic nerve impingement can be treated by setting a greater pull on the inpinged side and creating a distal/lateral force on the hip to maximize the opening up on the sciatic nerve. Further, a scoliosis condition may be treated by maximizing the force on the concave side of the major curve. The patient will be face down and blocked to maximize de-rotation. A superior anterior medical mobilization force is applied to the patient during the active traction portion of the treatment.

Figure 9:
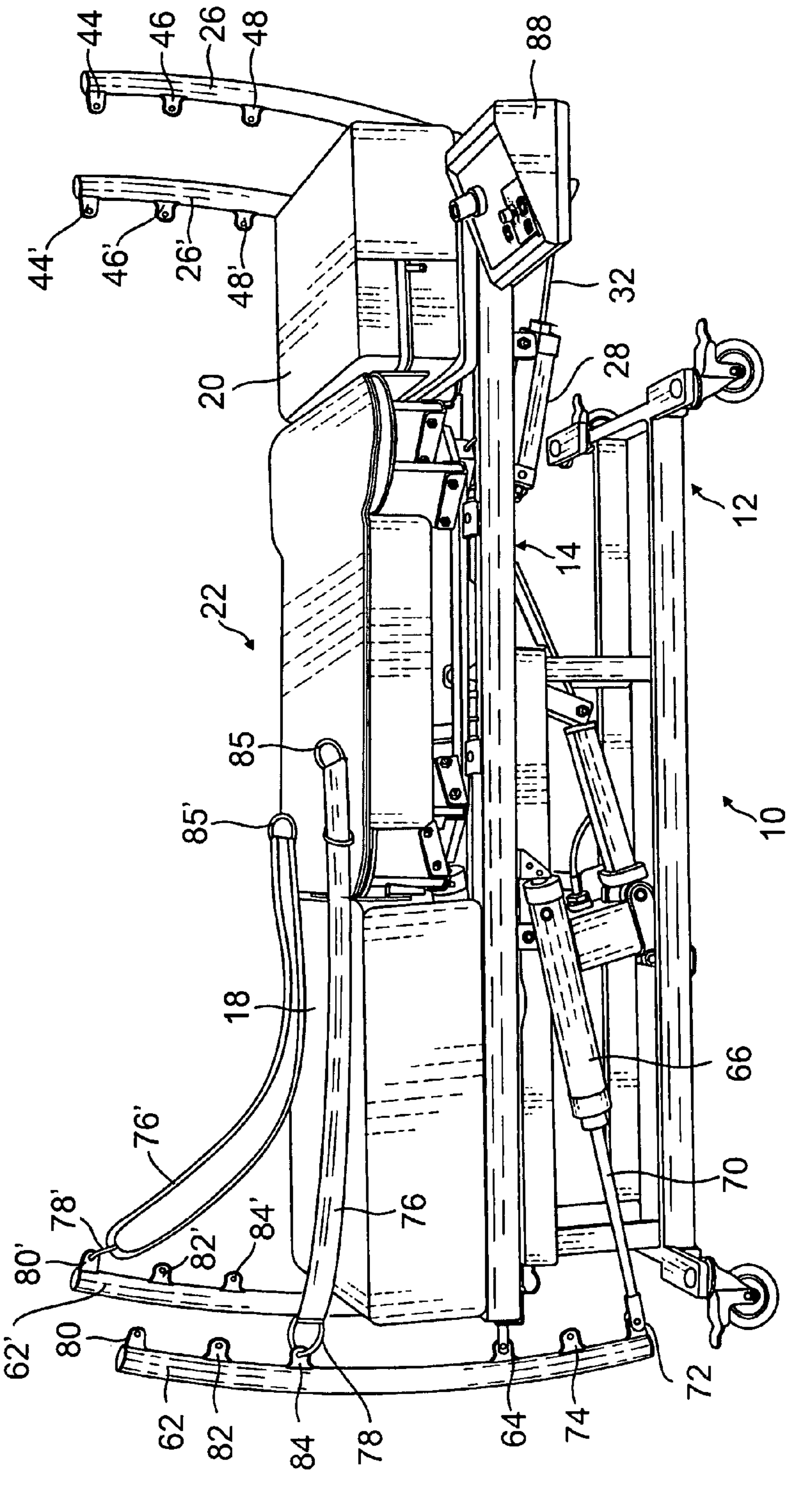
FIG. 9 is a perspective elevational view of a traction bed according to a second embodiment of the present invention.
Figure 10:
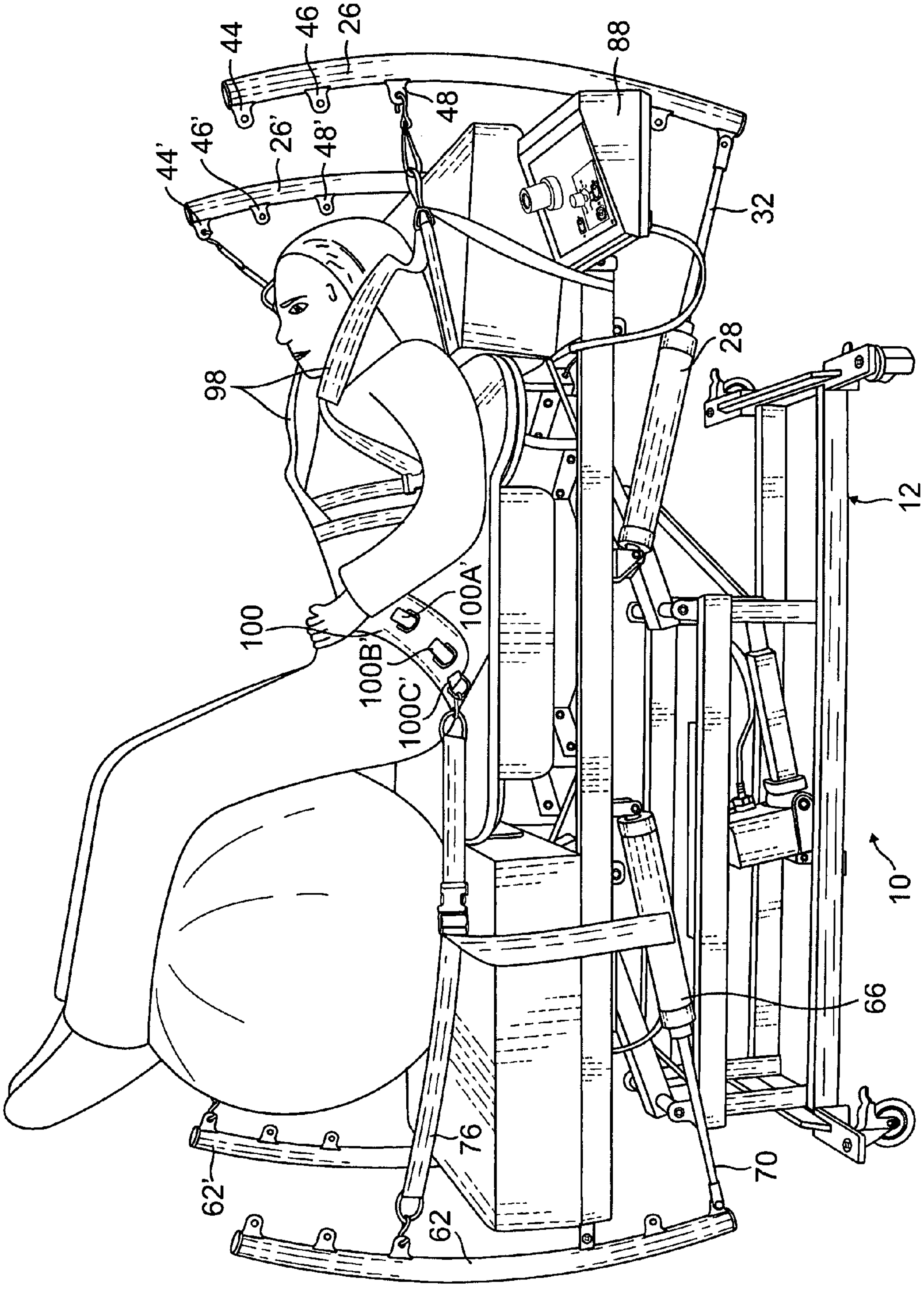
FIG. 10 is a perspective view of the second embodiment shown in FIG. 9 with a patient lying back down on the traction bed.

A second embodiment of the present invention is shown in FIGS. 9-10. In this second embodiment, the spreader bar 38 has been eliminated and a second pivot arm 26' has been mounted to the head end of the traction bed 10 as shown in FIGS. 9 and 10. This second embodiment is used in the same manner as the first embodiment except that now, the carabiner 58 is used for connecting one of the shoulder straps 98 to one of the attachment points 44, 46 and 48 on pivot arm 26 and the carabiner 60 is used for connecting the other shoulder strap 98 to one of the attachment points 44', 46' or 48' on pivot arm 26'.

While the fundamental novel features of the invention have been shown and described, it should be understood that various substitutions, modifications, and variations may be made by those skilled in the arts, without departing from the spirit or scope of the invention. Accordingly, all such modifications or variations are included in the scope of the invention as defined by the following claims:

I claim:

1. A traction bed comprising:

a base frame;

an elongate planar table having a longitudinal axis and attached to and supported by the base frame on which a patient may lie with a head disposed at a first end and feet disposed at a second end;

a vibration platform disposed in the planar table in alignment with the plane of the table;

vibration apparatus engaged with the vibration platform for selectively imparting a vibration motion to the vibration platform;

a pelvic belt for fitting around a pelvis of a patient;

the pelvic belt having a first "D" ring disposed on one lateral side of the pelvic belt and a second "D" ring disposed on the other lateral side of the pelvic belt;

a first strap connected to the first "D" ring;

a second strap connected to the second "D" ring;

a first means for selectively applying a tension force to the first strap in a direction toward the second end of the planar table;

a second means for selectively applying a tension force to the second strap in a direction toward the second end of the planar table;

a chest harness for fitting around a chest of the patient and having a first shoulder strap disposed on one lateral side of the chest harness and a second shoulder strap disposed on the other lateral side of the chest harness;

a third means connected to the first shoulder strap for selectively applying a tension force to the first shoulder strap toward the first end of the planar table;

a fourth means connected to the second shoulder strap for selectively applying a tension force to the second shoulder strap toward the first end of the planar table; and a controller means connected to the vibration apparatus for activating the vibration apparatus and connected to each of the first, second, third and fourth means for applying a tension force to the first and second straps and the first and second shoulder straps respectively.

2. The traction bed according to claim 1 wherein:

the first means includes: a first pivot arm pivotally connected to the second end of the planar table adjacent a first lateral edge of the planar table for pivotal movement in the longitudinal direction outwardly and away from the second end and pneumatic means connected to the controller for selectively pivoting the first pivot arm; and the second means includes a second pivot arm pivotally connected to the second end of the planar adjacent a second lateral edge of the planar table for pivotal movement in the longitudinal direction outwardly and away from the second end and pneumatic means connected to the controller for selectively pivoting the second pivot arm.

3. The traction bed according to claim 2 wherein the first pivot arm and second pivot arm are pivotally moved together in unison.

4. The traction bed according to claim 2 wherein:

the third means includes a third pivot arm pivotally connected to the first end of the planar table adjacent the first lateral edge of the planar table for pivotal movement in the longitudinal direction outwardly and away from the first end and pneumatic means connected to the controller for selectively pivoting the third pivot arm; and the fourth means includes a fourth pivot arm pivotally connected to the first end of the planar table adjacent the second lateral edge of the planar table for pivotal movement in the longitudinal direction outwardly and away from the first end and pneumatic means connected to the controller for selectively pivoting the fourth pivot arm.

5. The traction bed according to claim 4 wherein the third pivot arm and fourth pivot arm are pivotally moved together in unison.

6. A traction bed comprising:

a base frame;

an elongate planar table having a longitudinal axis and attached to and supported by the base frame on which a patient may lie with a head disposed at a first end and feet disposed at a second end;

a vibration platform disposed in the planar table in alignment with the plane of the table;

vibration apparatus engaged with the vibration platform for selectively imparting a vibration motion to the vibration platform;

a first and second pivot arms disposed at the second end of the planar table;

a first connector for pivotally connecting the first pivot arm to the planar table adjacent a lateral edge of the planar table for pivotal movement in the longitudinal direction outwardly and away from the second end; and a second connector for pivotally connecting the second pivot arm to the planar table adjacent an opposite lateral edge of the planar table for pivotal movement in the longitudinal direction outwardly and away from the second end;

the first and second connectors connected to their respective pivot arms at a position intermediate the ends of the pivot arms dividing each pivot arm between an upper portion of the pivot arm and a lower portion of the pivot arm;

a first pneumatic means attached between the base frame and the lower portion of the first pivot arm for selective pivoting the first pivot arm;

a second pneumatic means attached between the base frame and the lower portion of the second pivot arm for selective pivoting the second pivot arm;

a pelvic belt for fitting around a pelvis of the patient;

the pelvic belt having a first "D" ring disposed on one lateral side of the pelvic belt facing the first pivot arm and a second "D" ring disposed on the other lateral side of the pelvic belt facing the second pivot arm;

a strap connected between the upper portion of the first pivot arm and the first "D" ring;

a strap connected between the upper portion of the second pivot arm and the second "D" ring;

a third pivot arm disposed at the first end of the planar table;

a third connector for pivotally connecting the third pivot arm to the planar table adjacent the first end of the planar table for pivotal movement in the longitudinal direction outwardly and away from the first end;

the third connector connected to the third pivot arm at a position intermediate the ends of the third pivot arm dividing the third pivot arm between an upper portion and a lower portion of the third pivot arm;

a third pneumatic means attached between the base frame and the lower portion of the third pivot arm for selectively pivoting the third pivot arm a chest harness for fitting around a chest of the patient and having a first shoulder strap disposed on one lateral side and a second shoulder strap disposed on the other lateral side of the chest harness facing the third pivot arm;

a spreader bar having a fourth connector positioned intermediate the ends of the bar for swingably connecting the spreader bar to the upper portion of the third pivot arm;

means for connecting the first shoulder strap to a portion of the spreader bar on one side of the fourth connector and means for connecting the second shoulder strap to the spreader bar on the other side of the fourth connector; and a controller means connected to the vibration apparatus for activating the vibration apparatus and connected independently to each of the first, second and third pneumatic means for independently pivoting the first, second and third pivot arms.

* * * * *